(12) United States Patent
Koehler et al.

(10) Patent No.: US 12,165,325 B2
(45) Date of Patent: Dec. 10, 2024

(54) DEVICE AND METHOD FOR EVALUATING DARK FIELD IMAGES

(71) Applicant: KONINKLIJKE PHILIPS N.V., Eindhoven (NL)

(72) Inventors: Thomas Koehler, Norderstedt (DE); Michael Grass, Buchholz In der Nordheide (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 373 days.

(21) Appl. No.: 17/436,095

(22) PCT Filed: Mar. 12, 2020

(86) PCT No.: PCT/EP2020/056634
§ 371 (c)(1),
(2) Date: Sep. 3, 2021

(87) PCT Pub. No.: WO2020/182939
PCT Pub. Date: Sep. 17, 2020

(65) Prior Publication Data
US 2022/0189024 A1 Jun. 16, 2022

(30) Foreign Application Priority Data
Mar. 14, 2019 (EP) .................................... 19162802

(51) Int. Cl.
*G06T 7/00* (2017.01)
*A61B 6/00* (2024.01)
(Continued)

(52) U.S. Cl.
CPC ............ *G06T 7/0016* (2013.01); *A61B 6/032* (2013.01); *A61B 6/4035* (2013.01);
(Continued)

(58) Field of Classification Search
None
See application file for complete search history.

(56) References Cited

U.S. PATENT DOCUMENTS

| 2016/0038232 | A1* | 2/2016 | Brannan | ............ | A61B 18/1815 |
| | | | | | 29/828 |
| 2017/0225015 | A1* | 8/2017 | Thieme | ................ | A61B 6/4258 |

(Continued)

FOREIGN PATENT DOCUMENTS

| BR | 102017002683 A2 | 10/2018 |
| EP | 2777590 A1 | 9/2014 |

OTHER PUBLICATIONS

Dynamic In Vivo Chest X-ray Dark-Field Imaging in Mice R. Gradl, K. S. Morgan, M. Dierolf, C. Jud, L. Hehn, B. Günther, W. Möller, D. Kutschke, L. Yang, T. Stoeger, D. Pfeiffer, B. Gleich, K. Achterhold, O. Schmid, and F. Pfeiffer (Year: 2018).*

(Continued)

*Primary Examiner* — Nancy Bitar
(74) *Attorney, Agent, or Firm* — Larry Liberchuk

(57) ABSTRACT

The present invention relates to the use of dark field X-ray images in an ablation treatment of a tumour. By acquiring dark field X-ray images displaying the region of interest targeted in the ablation treatment, information can be derived which allows taking a decision on terminating the ablation treatment. A set of dark field X-ray images is received (101), which is acquired at different time instants and comprises the region of interest. Dark field X-ray images of the set are compared (102), for example by determining difference images between the individual images. If during that comparison a change in the dark field X-ray images is detected over time in the region of interest, then a signal is generated (103) indicating a change has occurred. That signal may indicate that healthy tissue is (Continued)

being affected instead of the tumour and that consequently the ablation treatment should be ended.

11 Claims, 3 Drawing Sheets

(51) Int. Cl.
  *A61B 6/03* (2006.01)
  *A61B 6/40* (2024.01)
  *A61B 6/42* (2024.01)
  *A61B 18/14* (2006.01)
  *G06T 7/11* (2017.01)
  *G06T 7/30* (2017.01)
  *A61B 18/00* (2006.01)
  *A61B 18/02* (2006.01)

(52) U.S. Cl.
  CPC ............ *A61B 6/4291* (2013.01); *A61B 6/486* (2013.01); *A61B 6/5264* (2013.01); *A61B 18/1477* (2013.01); *G06T 7/11* (2017.01); *G06T 7/30* (2017.01); *A61B 2018/00541* (2013.01); *A61B 2018/00577* (2013.01); *A61B 2018/0293* (2013.01); *G06T 2207/10081* (2013.01); *G06T 2207/10116* (2013.01); *G06T 2207/20224* (2013.01); *G06T 2207/30061* (2013.01); *G06T 2207/30096* (2013.01)

(56) References Cited

U.S. PATENT DOCUMENTS

| | | | |
|---|---|---|---|
| 2018/0140269 A1* | 5/2018 | Roessl | A61B 6/032 |
| 2018/0271465 A1* | 9/2018 | Proksa | G16H 50/30 |
| 2018/0279973 A1 | 10/2018 | Schaefer | |
| 2019/0293577 A1* | 9/2019 | Horiba | G01N 23/20025 |
| 2021/0401502 A1* | 12/2021 | Liu | A61B 18/082 |

OTHER PUBLICATIONS

PCT International Search Report, International application No. PCT/EP2020/056634, Jul. 3, 2020.
Gradl R. et al., "Dynamic In Vivo Chest X-Ray Dark-Field Imaging in Mice", IEEE Transactions on Medical Maging, vol. 38, No. 2, Sep. 6, 2018 (Sep. 6, 2018), pp. 649-656, XP055557867.
Willer K. et al., "X- Ray Dark-Field Imaging of the Human Lung—A Feasibility Study on a Deceased Body", PLoS One, vol. 13, No. 9, Sep. 27, 2018 (Sep. 27, 2018), p. e0204565, XP055625547.
Scherer K. et al., "X-Ray Dark-Field Radiography—In-Vivo Diagnosis of Lung Cancer in Mice", Scientific Reports 7:402, 2017.

* cited by examiner

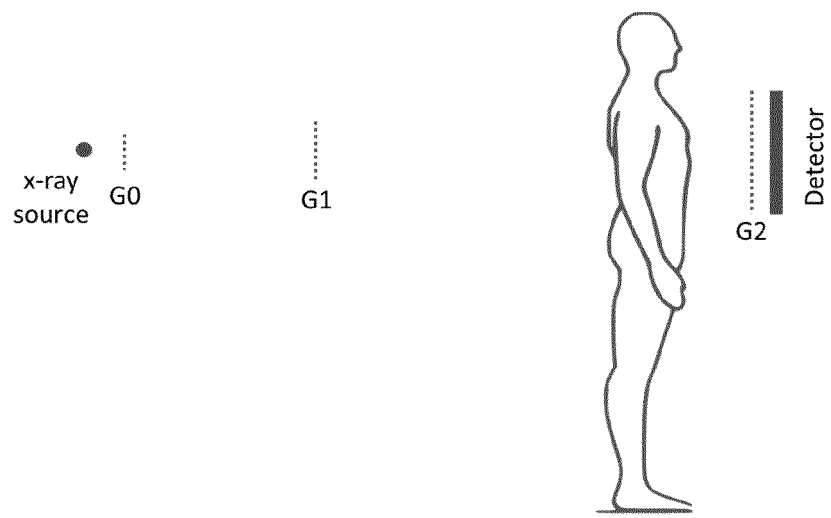
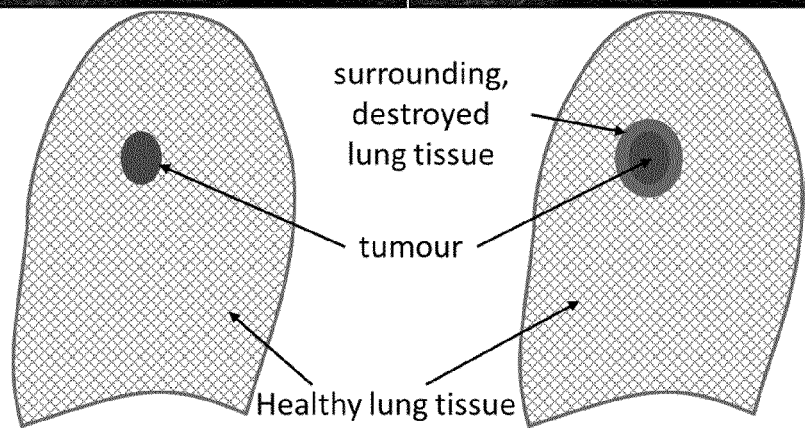
Fig.2

DEVICE AND METHOD FOR EVALUATING DARK FIELD IMAGES

FIELD OF THE INVENTION

The present invention is generally related to the field of methods and devices for monitoring dark field X-ray images obtained during an ablation treatment.

BACKGROUND OF THE INVENTION

Lung cancer is known to be a main cause of cancer deaths. Mostly, lung cancer is diagnosed at an advanced stage with poor prognosis. There is a constant drive towards the development.

A common treatment option for lung cancer is transbronchial or transthoracic RF ablation, whereby part of the electrical conduction system of the tumour is ablated using the heat generated by the applied RF signal. For transbronchial interventions a bronchoscope with a needle is navigated through the bronchi towards the tumour and the needle tip is inserted in the tumour tissue. For transthoracic therapy a needle is inserted through the thorax into the tumour tissue. Subsequently, the tumour is destroyed using RF energy deposition.

A particular problem in tumour ablation is to end the procedure at the right time. If the treatment is ended too early, the tumour is not completely destroyed. On the other hand, if stopped too late, healthy surrounding tissue is damaged.

Hence, there is a need for obtaining more information that can serve as a basis for deciding on when to stop an ablation treatment.

SUMMARY OF THE INVENTION

It is an object of embodiments of the present invention to provide for a way to obtain an indication of when to end an ablation treatment.

The above objective is accomplished by the solution according to the present invention.

In a first aspect the invention relates to a device, configured to, during an ablation treatment targeted at a certain region of interest, acquire a set of dark field X-ray images at least comprising that region of interest at two or more time instants. By monitoring the evolution of the so obtained dark field X-ray images it is possible to detect a change over time in the region of interest. When a change is found when comparing dark field X-ray images of the acquired set, a signal indicating occurrence of said change is generated. The existence of this signal can serve as a basis for a decision on ending the ablation procedure.

In a another aspect the invention relates to a corresponding method.

The proposed solution indeed allows for obtaining relevant information to decide on continuing the ablation process or not. The invention capitalizes on the acquisition of dark field X-ray images comprising a region of interest, e.g. a tumour and the surrounding tissue during the ablation process. Dark field imaging as such is a modality which recently has gained attention since its potential for diagnostic purposes has been recognized. The inventors have found that the application of dark field X-ray imaging also offers benefits in an interventional context. More in particular, in the context of a treatment of a tumour, there is little or no change in the dark field image of the tumour when performing the ablation. However, healthy lung tissue displays a change in the dark field image once it is heated during the procedure. So, the difference in effect can be made visible when using dark field X-ray imaging. Consequently, the proposed method provides useful information about the appropriate time to terminate the ablation treatment.

In embodiments of the invention a determination of a difference image between at least some of the dark field X-ray images of the set is performed when comparing the images. The difference images provide a quantitative measure of any change, if present, and so allow taking a decision on bringing the procedure to an end. Optionally, a certain threshold level can be set and if the difference image contains one or more pixels exceeding that threshold level, the signal signalling the change may be generated. The existence of such signal can be used as a contribution of information to decide on ending the ablation procedure or not.

In embodiments a segmentation of the area corresponding to the region of interest is performed in the set of dark field X-ray images. Doing so increases the accuracy of the comparison. Segmentation algorithms are commonly known in the art and readily available.

In certain embodiments the method for evaluating dark field X-ray images comprises performing a motion compensation on one or more of the dark field images prior to the comparing. In this way the effect of motion can be reduced or even eliminated before performing the actual comparison. Motion could for example be caused by the respiration of the patient from whom the dark field X-ray images are made. Reducing or eliminating this effect contributes in obtaining more accurate comparisons of the dark field images.

The invention also relates to a program, executable on a programmable device containing instructions, which, when executed, perform the method as described, and to a computer readable medium whereon the program is stored.

In one aspect the invention relates to a method for managing an ablation treatment directed towards a region of interest, the method comprising:
  initiating an ablation treatment of said region of interest,
  acquiring during the ablation treatment dark field X-ray images comprising the region of interest,
  evaluating as set out previously the acquired dark field X-ray images acquired at at least two different time instants,
  receiving in a control device a signal indicating occurrence of a change in the region of interest of the dark field X-ray images, said change being detected during said evaluating,
  ending via the control device the ablation treatment.

In another aspect the invention relates to a device for evaluating dark field X-ray images acquired during an ablation treatment directed towards a region of interest present in said dark field X-ray images. The device comprises:
  an image receiver for receiving a set of dark field X-ray images acquired at a first time instant and at least a second time instant and comprising said region of interest,
  a comparator for performing a comparison of dark field X-ray images of said set at said first time instant and at least said second time instant,
  a signal generator for generating a signal indicating occurrence of a change in said dark field X-ray images acquired at said first time instant and at least said second time instant if said change is detected in said region of interest during said comparison.

For purposes of summarizing the invention and the advantages achieved over the prior art, certain objects and advantages of the invention have been described herein above. Of course, it is to be understood that not necessarily all such objects or advantages may be achieved in accordance with any particular embodiment of the invention. Thus, for example, those skilled in the art will recognize that the invention may be embodied or carried out in a manner that achieves or optimizes one advantage or group of advantages as taught herein without necessarily achieving other objects or advantages as may be taught or suggested herein.

The above and other aspects of the invention will be apparent from and elucidated with reference to the embodiment(s) described hereinafter.

BRIEF DESCRIPTION OF THE DRAWINGS

The invention will now be described further, by way of example, with reference to the accompanying drawings, wherein like reference numerals refer to like FIG. 1 illustrates the use of gratings in dark field X-ray imaging.

FIG. 2 illustrates the appearance of the tumour and the surrounding tissue before and at the end of the ablation.

DETAILED DESCRIPTION OF ILLUSTRATIVE EMBODIMENTS

Figure 3:
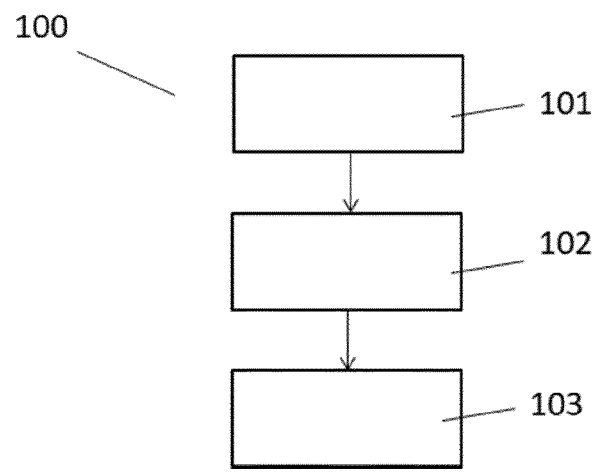
FIG. 3 illustrates a flow chart of the method according to an embodiment of the invention.

The present invention will be described with respect to particular embodiments and with reference to certain drawings but the invention is not limited thereto but only by the claims.

Furthermore, the terms first, second and the like in the description and in the claims, are used for distinguishing between similar elements and not necessarily for describing a sequence, either temporally, spatially, in ranking or in any other manner. It is to be understood that the terms so used are interchangeable under appropriate circumstances and that the embodiments of the invention described herein are capable of operation in other sequences than described or illustrated herein.

It is to be noticed that the term "comprising", used in the claims, should not be interpreted as being restricted to the means listed thereafter; it does not exclude other elements or steps. It is thus to be interpreted as specifying the presence of the stated features, integers, steps or components as referred to, but does not preclude the presence or addition of one or more other features, integers, steps or components, or groups thereof. Thus, the scope of the expression "a device comprising means A and B" should not be limited to devices consisting only of components A and B. It means that with respect to the present invention, the only relevant components of the device are A and B.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to one of ordinary skill in the art from this disclosure, in one or more embodiments.

Similarly it should be appreciated that in the description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the detailed description are hereby expressly incorporated into this detailed description, with each claim standing on its own as a separate embodiment of this invention.

Furthermore, while some embodiments described herein include some but not other features included in other embodiments, combinations of features of different embodiments are meant to be within the scope of the invention, and form different embodiments, as would be understood by those in the art. For example, in the following claims, any of the claimed embodiments can be used in any combination.

It should be noted that the use of particular terminology when describing certain features or aspects of the invention should not be taken to imply that the terminology is being re-defined herein to be restricted to include any specific characteristics of the features or aspects of the invention with which that terminology is associated.

In the description provided herein, numerous specific details are set forth. However, it is understood that embodiments of the invention may be practiced without these specific details. In other instances, well-known methods, structures and techniques have not been shown in detail in order not to obscure an understanding of this description.

The present invention extends the application domain of dark field X-ray imaging techniques to interventional scenarios. More in particular, the invention proposes the use of dark field X-ray imaging in the context of monitoring the treatment of diseases, e.g. lung diseases, and more in particular for obtaining information on when to terminate a tumour ablation treatment.

Since the benefits of applying dark field imaging have been recognized for diagnostic purposes, the technique has already been applied successfully for diagnosing lung diseases like chronic obstructive pulmonary disease (COPD), pulmonary fibrosis, lung cancer, etc.

Dark field X-ray imaging relies on the use of a Talbot-Lau interferometer, whereby a number of gratings are added into the X-ray beam path. FIG. 1 provides an illustration. In the example shown three gratings are inserted into the optical path. Typically, G0 and G2 are absorber gratings and G1 is a phase grating. The dark field image signal is generated by changes in the refractive index on a micrometre scale. For lung imaging, the dark field X-ray signal is predominantly generated by the air-tissue interfaces in the alveoli. The X-ray dark field signal quantifies the small-angle scattering occurring in the lung at the air-tissue interfaces. This allows using dark field imaging for diagnosis of lung diseases, which change the alveoli properties or concentration in the lung.

Applying dark field X-ray imaging offers a tool to assess structural changes in the considered region of interest, as the contrast is created by ultra-small angle scattering at small microstructures. Dark field X-ray imaging is for example highly sensitive to distortions of the natural lung microanatomy. In healthy lung tissue pronounced air-tissue interfaces cause heavy X-ray scattering. However, in cancerous tissue the air-tissue volume ratio is reduced due to uncontrolled cell proliferation and loss of alveolar space and therefore X-ray scattering is strongly reduced. Information on the scatter properties of the lung can be retrieved by evaluating a setup-specific interference pattern. Hence, a tumour, which is solid, creates, when applying a dark field imaging technique, a negative contrast in the surrounding lung tissue, which scatters as a highly structured material a lot. This observation underlies the method for evaluating dark field images presented in this invention. FIG. 2 provides an illustration. In the bottom, a schematic cross-section of the lung at the start of the intervention is shown, while on the right, the situation is sketched once surrounding tissue is damaged, filled with fluid. Above, the appearance in the dark-field image is shown. On the top left, the tumour shows up as a dark spot in the lung. If surrounding tissue is damaged, the dark spot increases in size and it becomes even darker in the centre.

In embodiments of the present invention dynamic dark field image acquisitions are used to monitor the progress of the ablation treatment directed towards a certain region of interest. A flow chart of an embodiment of the proposed method 100 for evaluating dark field X-ray images is provided in FIG. 3. In 101 a set of dark field X-ray images is received acquired at at least two different time instants during the ablation treatment and comprising the region of interest. In 102 dark field images of that set are compared and in 103 a signal is generated indicating occurrence of a change detected over time in the images.

During the ablation a dataset is acquired of dark field X-ray images at different instants of time, whereby each image comprises at least the region of interest. In some embodiments an automatic 2D registration of the acquired images may be provided. In some embodiments a fluoroscopic acquisition is performed, whereby a continuous stream of X-ray images of at least the region of interest is obtained. For example, a sliding window dark field acquisition can be employed, wherein a continuous sequence of images is acquired with a periodic grid movement. For instance, the stepped grating can be moved periodically by 0/3, 1/3, and 2/3 of its grating period or 0/5, 2/5, 4/5, 1/5, and 3/5 of it grating period (compared to a reference position). Alternatively, it can be moved by 0/8, 3/8, 6/8, 1/8, 4/8, 7/8, 2/8, 5/8, or other sequences. In other embodiments the set of dark field images at different instants of time is obtained from a number of separate, non-continuous images.

The common model for the measured X-ray intensity as a function of the grating position x is $$I(x)=TI_0(1+DV_0 \cos(\phi+\psi_0+x/p))$$

where T, D, $\phi$ are the transmission, the dark-field and the differential phase signal caused by the object and $I_0$, $V_0$, $\psi_0$ are the blank-scan intensity, the fringe visibility and the fringe phase, respectively. All these quantities are typically quantities that vary on a per pixel basis. Finally, p denotes the grating period. Since the blank scan parameters are obtained by measurements without the object, these are known during the intervention and the task of phase retrieval is to estimate the parameters T, D, $\phi$. Three measurements at three different grating positions are sufficient to estimate these parameters, e.g. taken at positions 0, 1/3 of the grating period and 2/3 of the grating period. If these grating positions are cyclically used, then any three subsequent projections can be used for phase retrieval. Typically, some more grating positions (e.g. 5 or 8—see also above) are taken in order to stabilize the estimation process.

Figure 4:
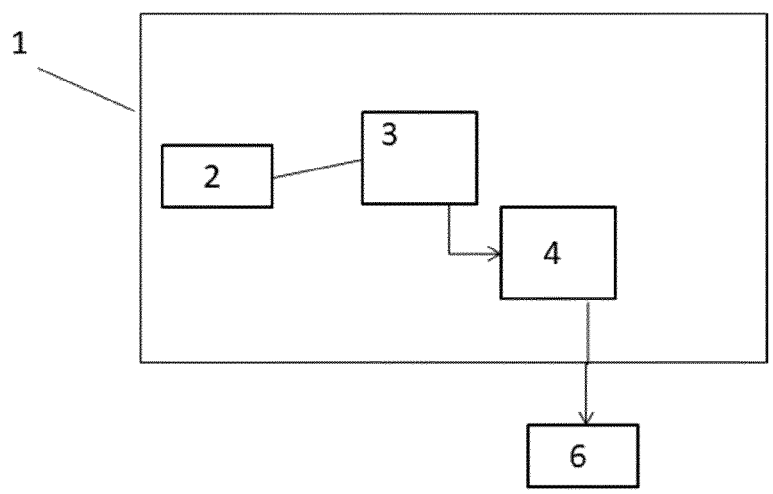
FIG. 4 illustrates an embodiment of a device for evaluating dark field X-ray images according to the invention.

An image receiver (2) of the device (1) for evaluating dark field X-ray images (see FIG. 4) is arranged to receive (101) the set of dark field X-ray images. A comparator (3) then performs a comparison (102) of the acquired dark field X-ray images. In some embodiments of the invention this involves determining difference images between the dark field X-ray images of the set. In embodiments of the invention the difference image is directly obtained by calculating a subtraction image of two dark field X-ray images. By making a difference image between pairs of images taken at different instants in time, a possible change over time in the region of interest can readily be made observable. In other embodiments a purely visual inspection of the various images is performed in order to monitor the evolution over time of the region of interest in the X-ray images. In yet other embodiments each image is evaluated independently, for instance by estimating a lesion size and next a comparison is performed of the estimated lesion sizes to check for changes over time of the lesion size.

The change over two (or more) time instants can for example be a change in the size of the lesion in the dark field image, e.g. a difference in size exceeding a predetermined threshold. As already mentioned above, there is hardly any change in the dark field signal of the tumour when treated because it is solid and remains solid. In contrast, once the ablation procedure starts destructing healthy lung tissue, the affected lung tissue generates less dark field signal. The destruction of the lung tissue causes damage of the thin walls of the alveoli, inflow of fluid and, as a consequence, a collapse of the alveoli. Thus, the damaged tissue does no longer create dark field signal and the size of the lesion in the dark field image increases. Consequently, by acquiring dark field X-ray images during the ablation and evaluating said images a contribution of information on the correct time to end the treatment can be obtained. This piece of information on a change in lesion size can be used next to other available information to make a final decision on ending the treatment.

The change may also be a shift in the shape of an object, e.g. the tumour, in the region of interest. This may occur, for instance, in case a vessel is going through a tumour which is heated, whereby lung tissue along the vessel gets damaged when the heat is transported away. This might lead to a line-like structure connected to the tumour. Again, a threshold level may be used to define from which difference in shape there is a change which should be indicated. The threshold level can be expressed based on one or more parameters that are indicative of the shape of the object.

In case a change over time is detected in the dark field X-ray images in the region of interest during the procedure, a signal is generated in a signal generator (4) to indicate the occurrence of that change. This signal can be transmitted to a device (6) controlling the ablation procedure. Based on reception of the signal the control device (6) can subsequently take the necessary action to end the ablation process. Alternatively or consecutively the signal can be transmitted to a further device that, upon receipt of the signal, can provide information, such as an image or text on a display or a sound from a speaker, allowing a decision on continuing the ablation process or not. This further device may also be the control device or be integrated with the control device.

In embodiments of the invention a segmentation is performed of the region of interest in the dark field images before starting the comparison. This may be beneficial for increasing the accuracy of the comparison. The dark field image segmentation can be automated, for example steered by a software program.

As the dark field images are acquired while a patient is undergoing the ablation treatment, it may happen that the patient's respiration causes some motion in the acquired X-ray images. Therefore it may be beneficial in some embodiments of the invention to perform a motion compensation on one or some of the dark field X-ray images prior to carrying out the comparison. Such motion compensation may comprises an alignment of a reference in the region of interest. The reference may be the tumour before treatment start.

In some embodiments the X-ray image is a dark field computed tomography image. Computed tomography combines a series of X-ray images taken from different angles and uses computer processing to create cross-sectional images. Also in these embodiments a grating-based approach can be adopted, whereby a three-grating interferometer is introduced into the X-ray beam path, so that the signal measured on the X-ray detector is sensitive to X–

In one aspect the invention also relates to a method to manage an ablation treatment directed towards a region of interest. The method comprises initiating an ablation treatment of the region of interest. The region of interest comprises the tumour to be treated and some surrounding tissue. The tumour can be identified in various ways, for example by bi-plane radiography, 3D computed tomography, magnetic resonance imaging, or alike. It may also start from a 2D-3D registration of an x-ray image with a 3D image (CT, MR).

Optionally a collimation is performed with a collimation unit to restrict the X-ray beam to the region of interest. Suitable gratings can be inserted, for example two absorber gratings and a phase grating in between the absorber gratings.

Before initiating the intervention a set of suitable angles can be selected to detect the tumour in the surrounding lung and a sequence of angles to be acquired during the ablation can be implemented. Suitable angles are a single or multiple angles which show the tumour in the dark field image with good contrast and well delineated with respect to the surrounding lung tissue. In case multiple angles are used, they are chosen in a way that the 3D shape of the tumour is well represented in the different projections, e.g. that a sufficient angular distance between the multiple angles is selected.

The actual ablation treatment of the region of interest can then be started. Safety margins can be set for safe tumour destruction pre-interventionally. For example, the ablation can be radiofrequency (RF) ablation or a laser ablation. Alternatively, cryo-ablation can be applied, whereby the tumour or tissue is destroyed using extreme cold.

Figure 5:
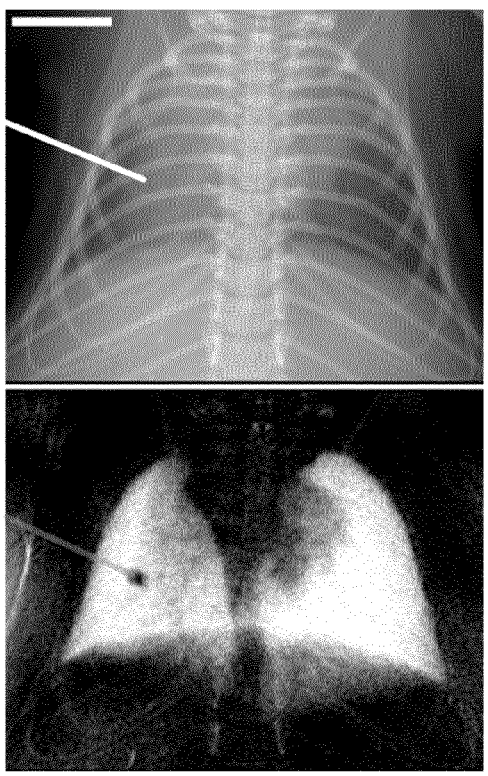
FIG. 5 illustrates the needle being visible in a transmission image (top) obtained along with a dark-field X-ray image or in the dark-field X-ray image itself (bottom).

By acquiring dark field X-ray images during the ablation the tumour can be made visible in 2D projections, which allows finetuning during the treatment the position of the needle and bronchoscope which have been navigated via the bronchial system to the tumour. Hence, the dark field image fluoroscopy enables real time guidance for the procedure. FIG. 5 shows a transmission image that always comes along with the dark-field image. In this image the needle is easily visible. So it can be segmented out and blended in into the dark-field image. The needle may also show up directly in the dark-field image as illustrated in the bottom part of the figure.

Once a set of dark field X-ray images has been collected, the evaluation method as set out above can be applied to the available dark field X-ray images. If appropriate, i.e. if a change over time is detected in the region of interest, a signal is generated to indicate a change has effectively occurred. This signal is received in a control device, which subsequently decides to end the ablation treatment. Further an automatic projection based estimation can be determined of the tumour margin destroyed during the ablation.

In one aspect the invention discloses a software program executable on a programmable device containing instructions, which, when executed, perform the method as previously described and to a computer readable medium whereon the program is stored.

While the invention has been illustrated and described in detail in the drawings and foregoing description, such illustration and description are to be considered illustrative or exemplary and not restrictive. The foregoing description details certain embodiments of the invention. It will be appreciated, however, that no matter how detailed the foregoing appears in text, the invention may be practiced in many ways. The invention is not limited to the disclosed embodiments.

Other variations to the disclosed embodiments can be understood and effected by those skilled in the art in practicing the claimed invention, from a study of the drawings, the disclosure and the appended claims. In the claims, the word "comprising" does not exclude other elements or steps, and the indefinite article "a" or "an" does not exclude a plurality. A single processor or other unit may fulfil the functions of several items recited in the claims. The mere fact that certain measures are recited in mutually different dependent claims does not indicate that a combination of these measures cannot be used to advantage. A computer program may be stored/distributed on a suitable medium, such as an optical storage medium or a solid-state medium supplied together with or as part of other hardware, but may also be distributed in other forms, such as via the Internet or other wired or wireless telecommunication systems. Any reference signs in the claims should not be construed as limiting the scope.

The invention claimed is:

1. A system for evaluating dark field X-ray images, comprising:
   a memory that stores a plurality of instructions; and
   a processor assembly coupled to the memory and configured to execute the plurality of instructions to:
      receive a set of dark field X-ray images acquired at a first time instant and at least a second time instant during an ablation treatment directed towards a region of interest present in the dark field X-ray images;
      perform a comparison of the dark field X-ray images in the set; and
      generate a signal indicating an occurrence of a change in the dark field X-ray images acquired at the first time instant and at least the second time instant if the change is detected in the region of interest during the comparison.

2. The system according to claim 1, wherein the processor assembly is configured to compare the dark field X-ray images in the set at the first time instant and at least the second time instant using a determination of a difference image between the dark field X-ray images of the set.

3. The system according to claim 1, wherein the processor assembly is further configured to segment the region of interest in the set of dark field X-ray images.

4. The system according to claim 1, wherein the change includes changing size or shape of an object in the region of interest.

5. The system according to claim 1, wherein the processor assembly is further configured to perform a motion compensation on one or more of the dark field X-ray images prior to the comparison.

6. The system according to claim 5, wherein the motion compensation comprises alignment of an object in the region of interest.

7. The system according to claim 1, wherein the dark field X-ray image is a dark field computed tomography image.

8. The system according to claim 1, wherein the set of dark field X-ray images is acquired using a plurality of gratings.

9. The system according to claim 1, wherein the ablation treatment is one of a laser ablation treatment, a radio frequency ablation treatment, and a cryo-ablation treatment.

10. A method for evaluating dark field X-ray images, comprising:
   receiving a set of dark field X-ray images acquired at a first time instant and at least a second time instant during an ablation treatment directed towards a region of interest present in the dark field X-ray images;
   performing a comparison of the dark field X-ray images in the set; and
   generating a signal indicating an occurrence of the change if during the comparison a change is detected in the region of interest in the dark field X-ray images acquired at the first time instant and at least the second time instant.

11. A non-transitory computer-readable medium for storing executable instructions, which cause a method to be performed to evaluate dark field X-ray images, the method comprising:
   receiving a set of dark field X-ray images acquired at a first time instant and at least a second time instant during an ablation treatment directed towards a region of interest present in the dark field X-ray images;
   performing a comparison of the dark field X-ray images in the set; and
   generating a signal indicating an occurrence of the change if during the comparison a change is detected in the region of interest in the dark field X-ray images acquired at the first time instant and at least the second time instant.

* * * * *